(12) United States Patent
Langsdorf et al.

(10) Patent No.: US 9,700,682 B2
(45) Date of Patent: Jul. 11, 2017

(54) DEVICE FOR RETAINING AND STORING LIQUID MEDIA AND METHOD OF EXPELLING THE LIQUID MEDIA

(71) Applicant: Schott AG, Mainz (DE)

(72) Inventors: Andreas Langsdorf, Ingelheim (DE); Inka Henze, Nieder-Olm (DE); Wolfram Beier, Essenheim (DE); Axel Ohlinger, Wiesbaden (DE)

(73) Assignee: Schott AG, Mainz (DE)

( * ) Notice: Subject to any disclaimer, the term of this patent is extended or adjusted under 35 U.S.C. 154(b) by 673 days.

(21) Appl. No.: 14/104,865

(22) Filed: Dec. 12, 2013

(65) Prior Publication Data

US 2014/0171901 A1 Jun. 19, 2014

(30) Foreign Application Priority Data

Dec. 13, 2012 (DE) .................. 10 2012 024 371
Dec. 2, 2013 (EP) .................. 13005587

(51) Int. Cl.
*A61M 5/32* (2006.01)
*A61M 5/00* (2006.01)
*A61M 5/24* (2006.01)

(52) U.S. Cl.
CPC .......... *A61M 5/3278* (2013.01); *A61M 5/001* (2013.01); *A61M 5/2429* (2013.01); *A61M 5/3232* (2013.01)

(58) Field of Classification Search
CPC ............ A61M 5/24; A61M 2005/2403; A61M 2005/2407; A61M 5/28; A61M 2005/2485; A61M 2005/2492; A61M 5/001; A61M 5/2429; A61M 5/3232; A61M 5/178; A61M 2005/1787; A61M 2005/3121
See application file for complete search history.

(56) References Cited

U.S. PATENT DOCUMENTS

| 2,549,417 A | 4/1951 | Brown |
| 3,811,441 A * | 5/1974 | Sarnoff .................. A61M 5/24 604/201 |
| 4,227,528 A * | 10/1980 | Wardlaw ............. A61M 5/2033 604/139 |

(Continued)

FOREIGN PATENT DOCUMENTS

| CN | 1020529 C | 5/1993 |
| DE | 697 28 062 T2 | 2/2005 |

(Continued)

OTHER PUBLICATIONS

Chinese Search Report dated Nov. 24, 2015 for Chinese Application No. 201310685201.5 (3 pages).

*Primary Examiner* — Quynh-Nhu H Vu
(74) *Attorney, Agent, or Firm* — Taylor IP, P.C.

(57) ABSTRACT

A device for retaining and storing a liquid medium, such as medication, includes a syringe body, a retention and/or storage container, consisting essentially of a glass material, a closure element for the retention and/or storage container consisting essentially of a rubber elastic material, and at least one needle. The retention and/or storage container is a vial having a solid bottom and a pushing device is provided to move the vial in a substantially axial direction in the syringe body, the pushing device acting upon the solid bottom of the vial.

13 Claims, 6 Drawing Sheets

AFTER EXPULSION

(56) References Cited

U.S. PATENT DOCUMENTS

| | | | |
|---|---|---|---|
| 4,767,413 A * | 8/1988 | Haber | A61M 5/326 604/198 |
| 4,772,271 A * | 9/1988 | Meyer | A61M 5/002 604/184 |
| 5,478,324 A | 12/1995 | Meyer | |
| 5,531,683 A * | 7/1996 | Kriesel | A61M 5/2429 604/416 |
| 5,807,323 A * | 9/1998 | Kriesel | A61M 5/14526 604/232 |
| 6,015,438 A * | 1/2000 | Shaw | A61M 5/3234 604/110 |
| 6,039,713 A * | 3/2000 | Botich | A61M 5/2429 604/110 |
| 6,190,364 B1 | 2/2001 | Imbert | |
| 6,569,115 B1 | 5/2003 | Barker et al. | |
| 6,981,963 B2 * | 1/2006 | Barker | A61M 5/326 604/191 |
| 8,679,068 B2 * | 3/2014 | Young | A61M 5/283 206/439 |
| 8,834,419 B2 * | 9/2014 | Jennings | A61M 5/2033 604/139 |
| 9,192,731 B2 | 11/2015 | Roberts et al. | |
| 2003/0199833 A1 * | 10/2003 | Barker | A61M 5/2429 604/197 |
| 2009/0259195 A1 | 10/2009 | Lin Lee | |
| 2010/0137809 A1 * | 6/2010 | Tschirren | A61M 5/24 604/187 |
| 2012/0004608 A1 * | 1/2012 | Lesch, Jr. | A61M 5/2033 604/135 |
| 2013/0018324 A1 * | 1/2013 | Reynolds | A61M 5/2466 604/195 |
| 2013/0197474 A1 * | 8/2013 | Bilton | A61M 5/2448 604/506 |

FOREIGN PATENT DOCUMENTS

| | | |
|---|---|---|
| EP | 1 600 190 A1 | 11/2005 |
| WO | 99/47194 A1 | 9/1999 |
| WO | 2010/100244 A1 | 9/2010 |
| WO | 2011/106870 A1 | 9/2011 |
| WO | 2012/000832 A1 | 1/2012 |
| WO | 2012/000838 A2 | 1/2012 |

* cited by examiner

Fig.4  SHORTLY BEFORE EXPULSION

Fig.5

AFTER EXPULSION

DEVICE FOR RETAINING AND STORING LIQUID MEDIA AND METHOD OF EXPELLING THE LIQUID MEDIA

BACKGROUND OF THE INVENTION

1. Field of the Invention

The present invention relates to a device for retaining and storing liquid media, for example medications, and a method for expelling liquid media from a device for retaining and/or storing liquid media.

2. Description of the Related Art

Syringes, in particular glass syringes which serve to retain and store liquid media, have become known from the state of the art. EP 1 600 190 A1 and U.S. Pat. No. 6,190,3564 describe a syringe body for retaining and/or storing a liquid medium, for example a medication which was placed into the syringe body, whereby the syringe body which serves to store or respectively retain the fluid is closed off at one distal end, sealing it. In EP 1 600 190 A1 and U.S. Pat. No. 6,190,364 a sealing cap is screwed onto a fastening ring for injecting the injection fluid and a syringe needle is secured to the fastening ring and thereby to the syringe body in such a way that a needle opening extending through the syringe needle has a flow connection with the distal opening of the syringe body. The disadvantage of the containers for retaining or respectively storing of liquid medications according to EP 1 600 190 A1 and respectively U.S. Pat. No. 6,190,364 is that, after the syringe fluid is expelled through the needle from the syringe body, the needle protrudes beyond the syringe body and the spent syringe bodies with the protruding needle represented an injury risk.

Hypodermic syringes whose needles still protrude after use can lead to pricks resulting in subsequent treatment of especially hospital personnel.

A device is known from U.S. Pat. No. 6,015,438 for a plastic syringe which cannot be used as a storage and retention container for medications whereby a syringe needle can be retracted into the syringe after use. According to U.S. Pat. No. 6,015,438 it was disadvantageous that the system specified in U.S. Pat. No. 6,015,438 had to be filled prior to being administered, since the plastic material of the syringe according to U.S. Pat. No. 6,015,438 was not suitable for extended storage of medications. Moreover, in the system according to U.S. Pat. No. 6,015,438 many different components are used which are in direct contact with the medication and which require certification. It is furthermore disadvantageous that the needle must be retracted into a plunger rod. This requires a hollow plunger rod.

DE 697 28 062 describes a possibility to retain a needle in such a way that it only punctures a septum after removal of the cap and does therefore not have any contact with the medication until it is used. It is also disadvantageous herein that the plunger rod must be especially designed in order to accommodate the needle after use of the syringe.

A device for administering a medication has become known from WO 2010/100244 whereby when expelling the medication first a seal member is punctured, preferably by a needle. Once the medication has been completely expelled, the needle can again be retracted into the syringe body by means of the plunger with which the medication was expelled. However, this does not occur automatically after delivery, but the needle must be actively retracted into the plunger. An additional problem in WO 2010/100244 is that a re-use cannot be ruled out with certainty.

WO 2012/000838 and WO 2012/000832 describe a syringe with which a medication can be administered via a needle. In WO 2012/000838 and WO 2012/000832 the medication is also pushed out from the storage container by means of a plunger. After expulsion of the medication, the needle with the entire receptacle is again retracted. The disadvantage of this system is on the one hand the relatively large space requirement and on the other hand that a multiple use cannot be entirely prevented, in addition to the large number of individual components.

A device has become from WO 2011/106870 wherein a septum is administered from a cartridge closed by a plunger. It is disadvantageous in WO 2011/106870 that the plunger is a separate component.

US 2009/0259195 A1 illustrates a syringe with a container which comprises a movable sealing ring. The displacement of the movable sealing ring has the disadvantage that a plurality of components must be sterilized. US 2009/0259195 A1 also describes a thrusting device which moves inside the hollow storage container.

A container is known from U.S. Pat. No. 2,549,417 with a closure element and a solid bottom which can be used in a syringe. Additionally, U.S. Pat. No. 6,015,438 illustrates a syringe with a needle retraction device.

What is needed in the art is a device to retain and store liquid media, for example medications, which overcomes the deficiencies and disadvantages of the existing art. The device should have a syringe body which on the one hand enables media to be retained, and on the other hand avoids the risk of injury, as for example in a system according to EP 1 600 190 A1. Moreover such a device should include as few contact pieces as possible for the medications.

SUMMARY OF THE INVENTION

The present invention provides a device for retaining and storing liquid media, for example medications, the device having a syringe body, a retention and/or storage container with a solid bottom, for example in the embodiment of a vial consisting, for example, essentially of a glass material, a cycloolefin copolymer (COC) or cycloolefin polymer (COP) for liquid media, a closure element for the storage and/or retention container which is formed, for example, of a rubber elastic material, as well as at least one needle and one needle retraction device.

In this application the term "vial" is to be understood to be a body which is open at least on one side. Therefore, a "vial" is a body which is open on one side—and has a solid bottom is suitable according to the present invention as a retention and/or storage container. A vial having two open ends is described as a cartridge. In contrast, an ampoule is a totally enclosed body. A glass ampoule has, for example, two fused ends. Whereas a glass ampoule cannot be used in the present invention, use of a cartridge would be possible if one of its open ends, for example on the bottom side of the cartridge, is sealed. An exemplary form of a retention and/or storage container which can be used in the current invention is a tubular body having a solid end.

According to the present invention, the device includes a pushing—for example a thrusting—device to move the retention and/or storage container in a substantially axial direction in the syringe body. By moving the entire retention and/or storage container the medication is expelled without having to move a plunger inside the retention and/or storage container. On the contrary, the thrusting device acts upon the bottom of the retention and/or storage container. Due to this measure there is no contact of the plunger with the medication, as for example in the case of WO 2012/000838, WO 2012/000832 or WO 2011/106870. The number of components which are in contact with the medication can thereby be considerably reduced. In contrast to the current state of the art, only two materials are still in direct contact with the medication, so that the device according to the present invention for retaining and storing of medications can more easily be sterilized. Moreover, due to the arrangement with a solid bottom the number of openings in the storage container is reduced, so that the number of seals, for example the moving parts such as plungers, is reduced. Such seals are always critical in regard to sterility and contact with the medications.

Materials which are used for the storage and retention container are, for example, materials which allow for long term storage of medications of at least three years. Exemplary materials include all glass and glass ceramic materials, but also polymer materials which are sufficiently durable, for example cycloolefin copolymer (COC) or cycloolefin polymer (COP).

For expulsion of the medication from the storage and/or retention container, the device according to the present invention includes a pushing device, for example a thrusting device, for moving the retention and/or storage container in a substantially axial direction in the syringe body.

The pushing- and/or thrusting device acts upon the bottom of the retention and/or storage container. After penetrating a stopper which seals the opening of the retention and/or storage container with the needle, the medication is expelled through movement of the storage container in the axial direction.

The thrusting device has, for example, at least one protrusion. When expelling the medication with the thrusting device the protrusion glides inside the syringe body, whereby the ends of the walls of the thrusting device, which is for example in the embodiment of a hollow cylinder with at least one opening, can act upon the container bottom, or respectively the solid bottom.

In one embodiment of the present invention, the protrusion is arranged in such a way that the thrusting device for moving the retention and/or storage container for delivery of the liquid medium abuts the retention and/or storage container.

In a further embodiment of the present invention, the protrusion is arranged in such a way that after expulsion of the liquid medium from the retention and/or storage container, the retention and/or storage container can be received in the thrusting device which is, for example in the embodiment of a hollow cylinder. For this purpose the protrusion locks in a recess in the wall of the syringe body, whereby the opening of the hollow cylinder is uncovered so that the retention and/or storage container can be received by the inside of the hollow cylinder after expulsion of the medication.

The syringe body moreover has a front end, whereby the needle retracting device is held in the front end, for example by a holding device. In order to release the needle retracting device it may be provided that the device includes a release mechanism for the needle retracting device, for example in the embodiment of a spring element, or in the embodiment of a claw.

In a first embodiment of the present invention, the needle retracting device includes a needle holding device and a compression spring.

The retention and/or storage container of the device for retaining and/or storing of liquid media, such as medications may be manufactured from a glass material and arranged, for example axially movable in the syringe body. We then have glass vials with a solid bottom. Exemplary glass materials are such glass materials which are approved as packaging material. A glass material of this type is, for example, the glass which is distributed by Schott AG, Mainz under the brand name FIOLAX™. The main components in the glass "FIOLAX™ clear" include 75 weight-% $SiO_2$, 10.5 weight-% $B_2O_3$, 5 weight-% $Al_2O_3$, 7 weight-% $Na_2O$ and 1.5 weight-% CaO. It has an average linear thermal coefficient of expansion α (20° C., 300° C.) of $4.9 \cdot 10^{-6}$/K, a transformation temperature Tg of 565° C. and a density ρ at 25° C. of 2.34 grams (g) per cubic centimeter ($cm^3$).

Due to the fact that the retention and/or storage container is arranged movable in the substantially axial direction in the syringe body, the retention and/or storage container can be moved, for example by a pushing or thrusting device, for example in the embodiment of a syringe plunger, and liquid medium which is present in the retention and/or storage container can be delivered through a needle. After the liquid has been completely expelled from the storage and/or retention container the needle retracting device can be activated and the needle can be completely retracted into the syringe body with the assistance of the needle retracting device.

In addition to the device, the present invention also specifies a method to deliver liquid medium, such as medications from a device for retention and/or storage. In the method of the present invention the closure of the retention and/or storage container is first opened by puncturing with a needle which is held, for example in a needle holding device. The liquid medium, in particular the medication then flows from the opened retention and/or storage container, whereby through axial movement of the retention and/or storage container in the syringe body the entire liquid medium can be expelled through the needle.

After extensive complete expulsion of the liquid medium, in particular the medication, the needle retraction device is then released, for example by a releasing mechanism, in such a way that the needle is retracted practically completely into the syringe body. The release mechanism may also serve to open a holding device on a needle holding device in such a way that, for example, a compression spring relaxes and that thereby the needle holding device together with the needle is retracted into the interior of the syringe body. The thrusting device for moving the retention and/or storage container may also be arranged in such a way that the thrusting device includes a hollow space which accommodates the retracted needle, as well as the retention and/or storage container which was pushed back in the axial direction together with the needle. The thrusting device is, for example, a hollow cylinder.

The needle holding device may be held at the front end of the syringe body, for example through a positive fit or friction connection and if the positive fit or friction connection of the holding device with the front end of the syringe body is neutralized by the release mechanism and if the needle retracting device is thereby released. By releasing the needle retracting device the compression spring relaxes and retracts the needle retracting device together with the needle into the interior of the syringe body.

In order to expel the liquid medium from the retention and/or storage container as completely as possible it is provided that the closure of the retention and/or storage container is closed with a rubber elastic material. This material can be compressed in such a manner that the liquid medium which is stored in the retention and/or storage container can to a large extent be completely expelled.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

Figure 1:
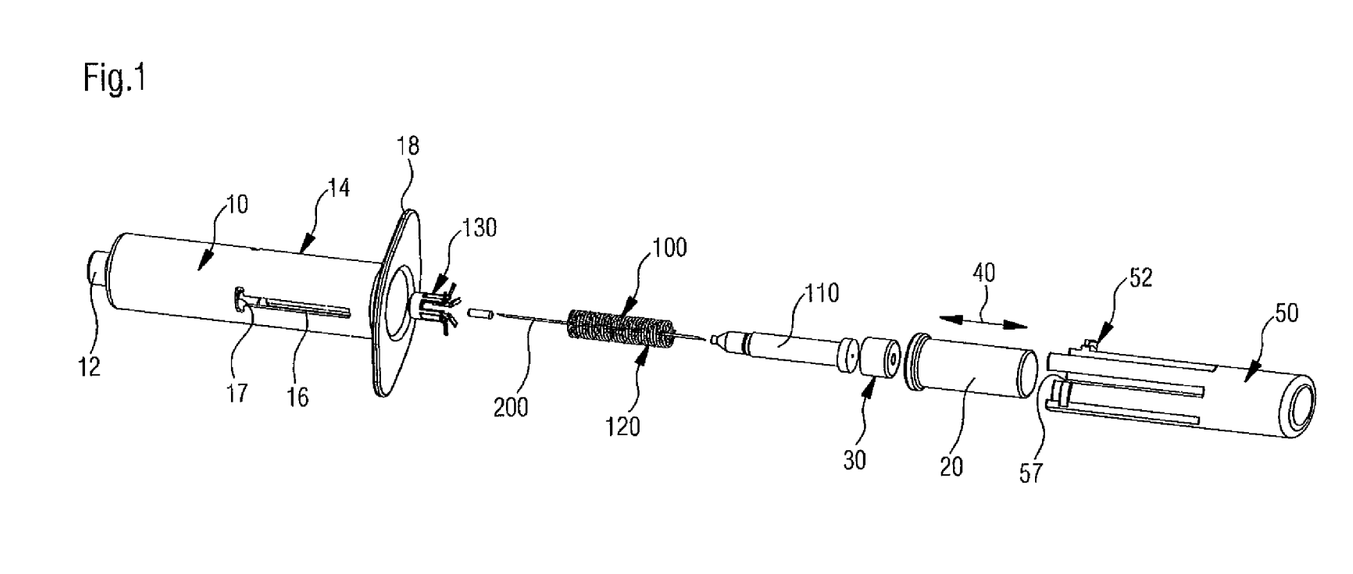
FIG. 1 is an elevation of one embodiment of a syringe body according to the present invention.

Referring now to the drawings, and more particularly to FIG. 1, there is illustrated the individual components of the inventive device for retaining and storing liquid media, in particular medications in a disassembled state. In an embodiment, however without restriction thereto, the device for retention and/or storage of liquid media includes a syringe body 10. Retention and/or storage container 20 which is manufactured, for example, of a glass material and which is closed with a stopper 30, such as one consisting essentially of a rubber elastic material, is placed movably in a substantially axial direction 40 into syringe body 10. Retention and/or storage container 20 with closure 30 can be moved inside syringe body 10 axially in direction 40 by a thrusting device 50 toward the front end of syringe body 10.

The device illustrated in detail in FIG. 1 moreover includes a needle retracting device 100. Needle retracting device 100 in turn includes a needle holding device 110, as well as a compression spring 120 and a release mechanism 130 in the embodiment of a claw. Compression spring 120 is guided by a spring guide which is provided through the needle holding device and which however is not absolutely required as an option.

Figures 7, 8:
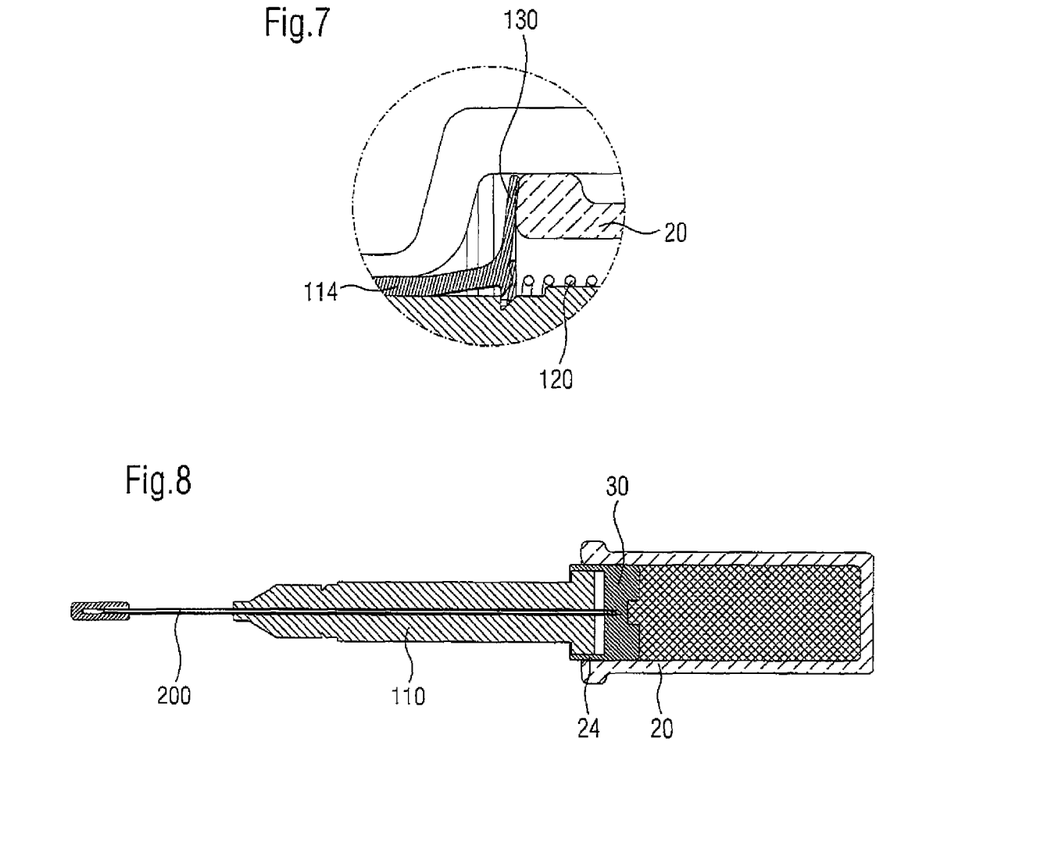
FIG. 7 is a detailed illustration of the release mechanism during activation in accordance with the present invention.
FIG. 8 is a sterile unit of the syringe body of the present invention.

Shown in a three-dimensional view in FIG. 1 are side views of individual parts. Syringe body 10 includes a front end or respectively a front region 12 into which needle holding device 110 through which needle 200 is guided can be inserted. Syringe body 10 which may be manufactured from a plastic moreover includes a region 14 with guide openings 16 which can accommodate protrusions 52 of thrust device 50 and which ensure that thrust device 50 is guided along openings 16 during axial movement in direction 40. In order to be able to handle the conventional processing machinery for filling, retention and storage of liquid media, syringe body 10 includes a syringe collar 18. Guide opening 16 moreover includes a recess 17 into which protrusions 52 can engage and release the inside 57 of the thrust body which is in the embodiment of a hollow body, in this case a hollow cylinder, so that storage and/or retention container 20 can be moved into this hollow space when retracting the needle, as shown in FIG. 7.

When the device for retaining and storing liquid media according to the present invention is being stored and the stored liquid is not to be expelled, the needle, for example injection needle 200 is not connected with syringe body 10. The needle, for example injection needle 200, may be produced from stainless steel. Release mechanism 130 is, for example in the embodiment of a claw formed of plastic. The needle holding device, which at the same time serves as a spring guide, is identified with reference number 110 and may consist of plastic. The compression spring which is part of the needle retracting device may be formed of spring steel. In order to enable extended storage of the liquid medium, in particular medication, the supply—or respectively storage and/or retention container—may be formed of a glass material, for example in a tube shape. Stopper 30, formed of a rubber elastic material, serves as the closure material for the tubular glass body in which the liquid, or respectively the medication, is accommodated. Thrusting device 50 for moving retention and/or storage container 20 in the substantially axial direction toward front end 12 is again manufactured from plastic and is equipped with at least one protrusion 52 for guidance purposes.

Figure 2:
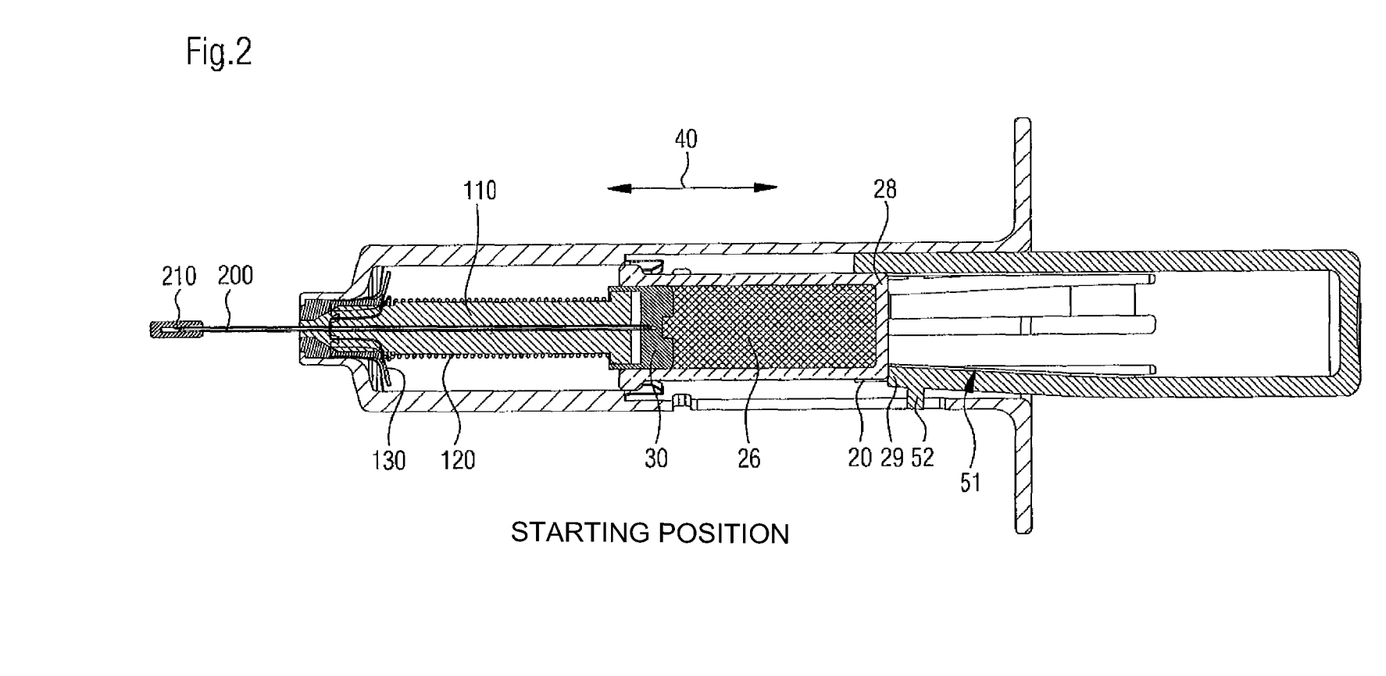
FIG. 2 illustrates the syringe body of FIG. 1 after placement of the needle and prior to expulsion of the liquid medium according to the present invention.

Referring now to FIG. 2, there is illustrated the inventive device for retaining and/or storing a medication in an assembled state in the starting position with needle 200 in place, but before expulsion of the fluid medium, in particular the medication which is contained in interior 26 of the glass storage and/or retention container.

The fill volume of the liquid medium, in particular medication in interior 26 of retention and/or storage container 20, amounts in the current example to for example 1 milliliter (mL), without being restricted thereto. At the end or respectively backside 28, or respectively the bottom of the storage and/or retention container, ends 29 of the wall, which are for example in the embodiment of fingers, fit against hollow thrusting device 50 which extends beyond syringe collar 18. As can be clearly seen in FIG. 2, backside 28 of the storage and/or retention container which is in the embodiment of a vial is a solid bottom upon which the thrusting device described below acts.

In the starting position in FIG. 2 protrusion 52 of the thrusting device is pushed downward, so that front section 51 of the thrusting device stops against the end or respectively backside 28 or respectively the bottom of the supply and/or storage container, so that the supply and/or storage container can be moved with the assistance of thrusting device 50 in axial direction 40 toward front end 12 of syringe body 10.

Also clearly visible is needle holding device 110 which is placed in front section 12 of the syringe body, whereby the needle holding device serves to guide the needle as well as at the same time also compression spring 120. Compression spring 120 is in tensioned condition in the starting position. Needle 200 is enclosed with a cap 210.

Needle 200, which is held inside the needle holding device, pierces the rubber elastic material of closure element 30 of retention and/or storage container 20 without penetrating through it.

Figure 3:
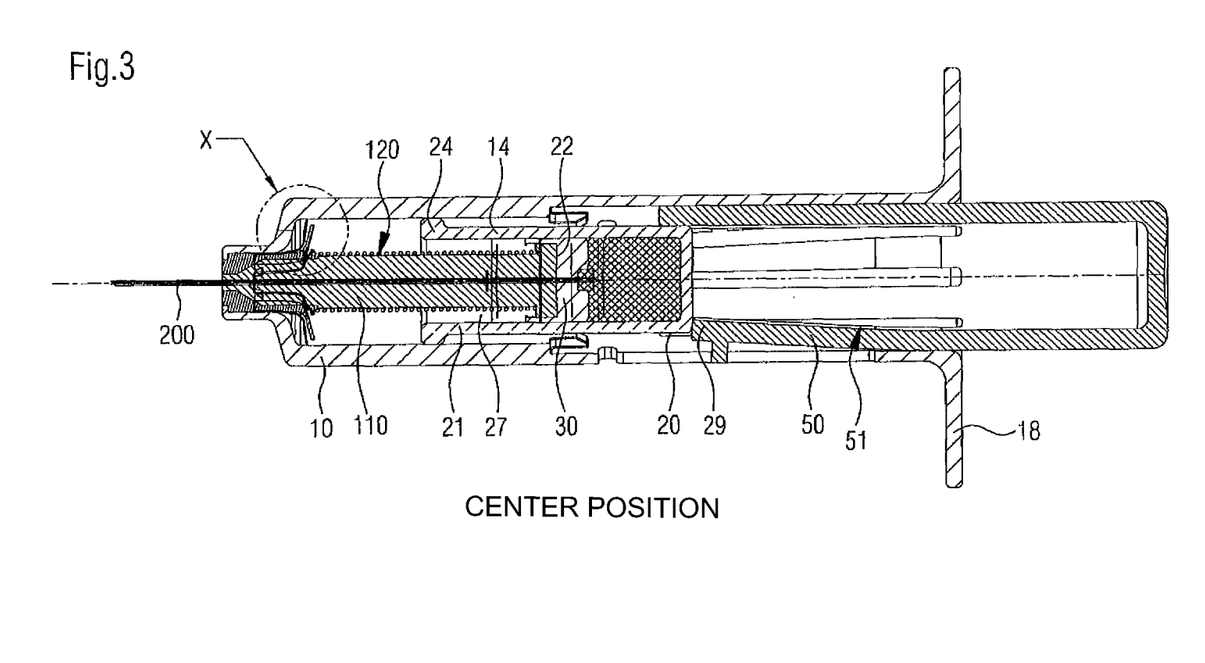
FIG. 3 illustrates the syringe body of FIG. 1 after placement of the needle into the storage and/or retention container and after expulsion of part of the liquid medium according to the present invention.

In order to expel the liquid or respectively the medication contained in interior 26 of the storage and/or retaining container 20, closure element 30 is punctured or respectively penetrated with the assistance of needle 200, as shown in FIG. 3. Same components as in FIGS. 1 and 2 are identified with the same reference numbers.

By punching through enclosure 30, the liquid inside container 20 can now be expelled through needle 200.

By moving depressed thrusting device 50 in axial direction 40 along guide groove 16 of the syringe body as illustrated in FIG. 1, the storage and/or retaining container is moved in the direction of front end 12 of syringe body 10, thereby expelling the liquid from interior 26.

Referring now to FIG. 3, there is shown the approximate center position of retention and/or storage container 20. As can be clearly seen in FIG. 3 the hollow retention and/or storage container is moved beyond closure element 30 with the assistance of thrusting device 50. Wall 21 of the retention and/or storage container is thereby moved between inside wall 14 of syringe body 10 as well as needle holding device 110 with compression spring 120. Guidance occurs hereby on the one hand through pressure of closure element 30 upon inside 22 of wall 21 of the hollow retention and/or storage container, as well as with assistance of guide protrusions 24 in wall 21 of the storage and/or retention container through inside wall 14 of syringe body 10.

A sufficient space 27 between inside wall 22 of the storage and/or retention container as well as compression spring 120 is hereby provided. Same components as in FIGS. 1 to 2 are identified in FIG. 3 with the same reference numbers.

Figure 4:
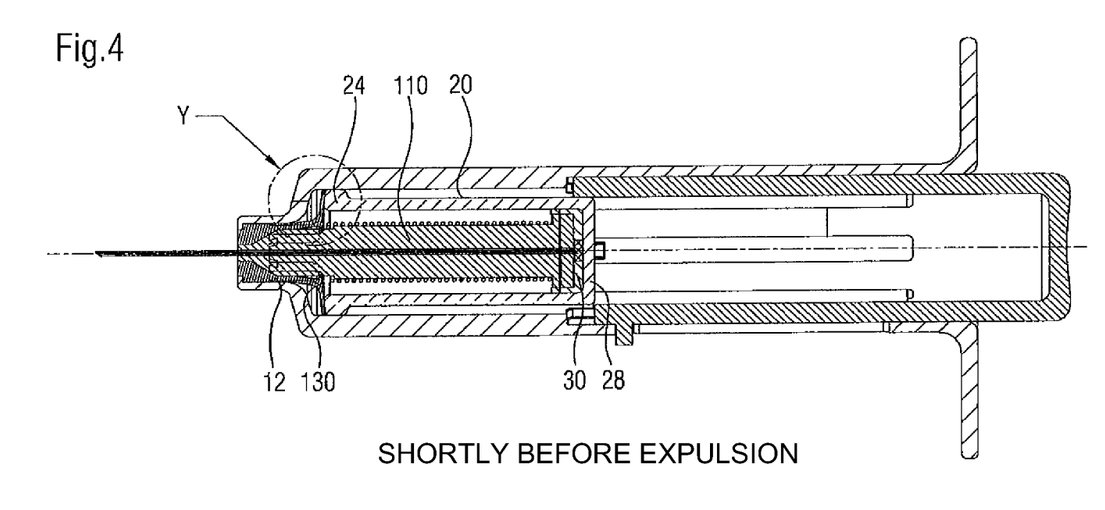
FIG. 4 illustrates the syringe body of FIG. 1 after expulsion of the entire liquid medium, however before activating the release mechanism according to the present invention.

FIG. 3 illustrates the device before release of the needle retraction device with assistance of the release mechanism in the embodiment of a claw 130. In FIG. 4 the end or respectively the back wall or respectively bottom 28 of the glass container abuts closure 30 and, with the exception of residue R, the complete content of the retention and/or storage container is expelled from interior 26 through needle 200.

The release of the needle retraction device with the assistance of the release mechanism is illustrated in detail in FIG. 4. For this purpose closure 30 consisting of a rubber elastic material is compressed with the assistance of thrusting device 50. On the one hand the still remaining residue R of the liquid medium, in particular the medication, is thereby further reduced. On the other hand, claw 130 is expanded due to protrusions 24 of retention and/or storage container 20. The positive fit of needle holding device 110 with the claw which is firmly connected with front end 12 of syringe body 10 is neutralized. Due to the pressure of the retention and/or storage container upon claw 130, the claw is expanded and the needle holding device is triggered or released.

Figure 5:
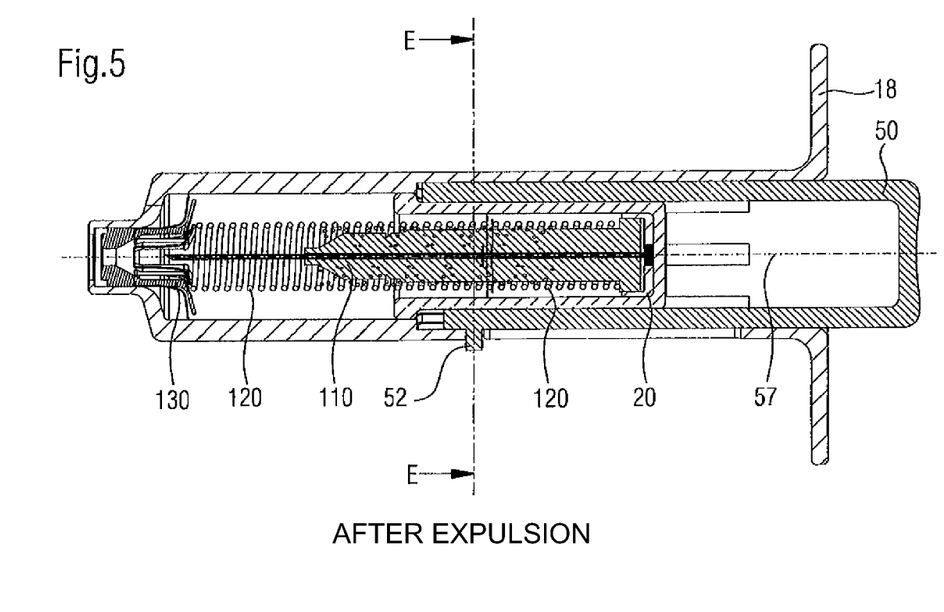
FIG. 5 illustrates the syringe body of FIG. 1 after activation of the release mechanism and the needle retracting device according to the present invention.

By neutralizing the positive fit or respectively friction connection between needle holding device 110 and front end 12 of the syringe body, compression spring 120 can relax, so that needle holding device 110 which is solidly or respectively insolubly connected with the needle, for example glued or pressed together, moves in the axial direction in the direction of syringe collar 18, as shown in FIG. 5.

Storage and/or retention container 20 returns together with needle holding device 110 into interior 57 of hollow thrusting device 50. This is possible since due to locking of collar 52 of the thrusting device in recess 17 of the syringe body the interior of the thrusting device is released to accommodate retention and/or storage container 20.

Retraction of the needle as well as of the storage and/or retention container 20 occurs through relaxation of the compression spring and the force acting upon closure element 30 during relaxation.

Same components as in FIGS. 1 to 4 are identified with the same reference numbers also in FIG. 5.

Figure 6:
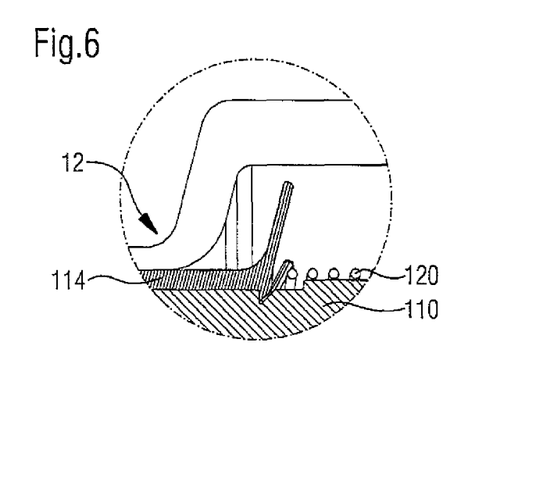
FIG. 6 is a detailed illustration of the release mechanism prior to activation according to the present invention.

In FIGS. 6 to 7, the release of the needle retraction device is illustrated in detail. Clearly visible is compression spring 120 which surrounds needle holding device 110.

The needle holding device is held by a positive fit in the region 114 of protrusion in the front region of the syringe body. The engagement with claw 130 which provides the positive connection to the needle holding body is firmly connected with the front region of the syringe body, for example through bonding. The needle holding body, or respectively the needle holding device, is thus held at front end 12 of syringe body 10.

The storage and/or retention container is identified with 20 in FIG. 7. If—as shown in FIG. 7—storage and/or retention container 20 is pressed against claw 130, then the claw is expanded and the positive connection in region 114 with needle holding body 110 is neutralized. The needle holding body is thus released and can—as shown in FIG. 5—move in the direction of the syringe interior due to the relaxation of spring 120.

FIG. 8 illustrates the components of the device which must be sterilized and together as a sterile unit are assembled with the remaining non-sterile components. The needle is kept sterile by the cap and the pierced closure until administered. Only the closure and the retention container are in contact with the medication until it is administered. Same components as in the previous Figs. are identified with the same reference numbers. These are needle 200, rubber stopper 30, storage and/or retention container 20 and needle holding device 110.

The present invention specifies for the first time a device for retaining and/or storing liquid media, for example medications, which can be expelled with a needle and which provides a needle retraction device, wherein the medication is in contact only with glass and rubber during storage and wherein no transferring of the media or additional assembly steps are required.

The invention includes aspects which are disclosed in the following clauses, which are part of the description but which are not claims:

1. A device for retaining and storing liquid media, such as medications includes a syringe body (10), a retention and/or storage container (20), consisting for example of a glass material, or a cycloolefin copolymer (COC) or a cycloolefin polymer (COP) for liquid media, having a closure element (30), for example in the form of a rubber elastic material, as well as at least one needle (200) and one needle retracting device (100).

The retention and/or storage container is in the embodiment of a vial having a solid bottom (28) and the device includes a pushing- or a thrusting device (50) to move the retention and/or storage container (20) in a substantially axial direction (40) in syringe body (10) wherein the pushing- or thrusting device acts upon solid bottom (28).

2. In the device according to clause 1, the thrusting device includes at least one protrusion (52).

3. In the device according to clause 2, the thrusting device has a hollow body, such as a hollow cylinder having at least one opening.
4. In the device according to one of the clauses 2 to 3, protrusion (52) is arranged such that thrusting device (50) for moving retention and/or storage container (20) for expulsion of the liquid medium abuts retention and/or storage container (20) in the region of the bottom of the retention and/or storage container.
5. In the device according to one of the clauses 2 to 4, protrusion (52) is arranged such that after expulsion of the liquid medium from the retention and/or storage container (20), retention and/or storage container (20) can be accommodated by the thrusting device (50), for example the hollow body, such as the hollow cylinder.
6. In the device according to one of the clauses 1 to 5, syringe body (10) has a front end (12) and a needle holding device (110) which is part of needle retracting device (100) and which is held in front end (12).
7. In the device according to one of the clauses 1 to 6, the device includes a release mechanism (130) for needle retracting device (100), such as a claw (130).
8. The device according to one of the clauses 1 to 7 provides that needle retracting device (100) includes needle holding device (110) and a compression spring (120).
9. A method for expelling liquid media, such as medications from a device for retention and/or storage according to one of the clauses 1 to 8, includes the following steps:
retention and/or storage container (20) in the embodiment of a vial having a solid bottom (28) is opened by puncturing a closure element (30) with a needle (200);
the liquid medium, in particular the medication, is delivered through needle (200) through axial movement of retention and/or storage container (20) in axial direction (40) in syringe body (10) with the assistance of a thrusting device (50) which acts upon solid bottom (28);
after practically complete expulsion of the liquid medium, in particular the medication needle, retracting device (100) is released in such a way that needle (200) is retracted to a great extent completely into syringe body (10) and
retention and/or storage container (20) is retracted into thrusting device (50).
10. The method according to clause 9 provides that the support of needle retracting device (100) at front end (12) of syringe body (10) is opened through a release mechanism (130), so that for example, a compression spring (120), is relaxed and a needle holding device (110) with needle (200) is pulled into the interior of syringe body (10).
11. The method according to one of the clauses 9 to 10 provides that a positive fit and/or friction connection of needle holding device (100) is neutralized through release mechanism (130) thereby releasing needle retraction device (100).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A device for retaining and storing liquid medium, the device comprising:
a syringe body;
a container which is at least one of a retention container and a storage container, said container being a vial having a solid bottom;
a closure element for said container;
at least one needle for expelling said liquid media from the device;
at least one needle retraction device coupled with said at least one needle and configured to pull said at least one needle back into said syringe body from an exposed position; and
a pushing device configured to move said container in a substantially axial direction in said syringe body and along at least a portion of said at least one needle by acting upon said solid bottom of said container.

2. The device according to claim 1, said container consisting essentially of one of a glass material, a cycloolefin copolymer (COC), and a cycloolefin polymer (COP).

3. The device according to claim 1, said pushing device being a thrusting device.

4. The device according to claim 1, said closure element consisting essentially of a rubber elastic material.

5. The device according to claim 3, said thrusting device including at least one protrusion.

6. The device according to claim 5, said thrusting device including a hollow body.

7. The device according to claim 6, said hollow body being a hollow cylinder having at least one opening.

8. The device according to claim 7, wherein said at least one protrusion is arranged such that said thrusting device for moving said container abuts said container for expulsion of the liquid medium in a region of a bottom of said container.

9. The device according to claim 8, said at least one protrusion being arranged such that after expulsion of the liquid medium from said container, said container is accommodated by said thrusting device.

10. The device according to claim 1, said syringe body having a front end and said needle retracting device including a needle holding device, wherein said needle holding device is positioned in said front end of said syringe body.

11. The device according to claim 10, further comprising a release mechanism for said needle retracting device.

12. The device according to claim 11, said release mechanism being a claw.

13. The device according to claim 1, said needle retracting device including a needle holding device and a compression spring.

* * * * *